US011185251B2

(12) United States Patent
Kametani

(10) Patent No.: US 11,185,251 B2
(45) Date of Patent: Nov. 30, 2021

(54) BIOLOGICAL SOUND ANALYZING APPARATUS, BIOLOGICAL SOUND ANALYZING METHOD, COMPUTER PROGRAM, AND RECORDING MEDIUM

(71) Applicant: PIONEER CORPORATION, Tokyo (JP)

(72) Inventor: Ryushin Kametani, Kawagoe (JP)

(73) Assignee: PIONEER CORPORATION, Tokyo (JP)

(*) Notice: Subject to any disclaimer, the term of this patent is extended or adjusted under 35 U.S.C. 154(b) by 553 days.

(21) Appl. No.: 16/073,320

(22) PCT Filed: Jan. 29, 2016

(86) PCT No.: PCT/JP2016/052830
§ 371 (c)(1),
(2) Date: Jul. 26, 2018

(87) PCT Pub. No.: WO2017/130415
PCT Pub. Date: Aug. 3, 2017

(65) Prior Publication Data
US 2019/0029562 A1 Jan. 31, 2019

(51) Int. Cl.
*A61B 5/08* (2006.01)
*A61B 7/04* (2006.01)
(Continued)

(52) U.S. Cl.
CPC .............. *A61B 5/0803* (2013.01); *A61B 5/08* (2013.01); *A61B 5/7275* (2013.01); *A61B 7/003* (2013.01);
(Continued)

(58) Field of Classification Search
CPC ........ G16H 50/30; A61B 5/0803; A61B 7/04; A61B 5/08; A61B 5/7275; A61B 7/003; A61B 2562/0204
See application file for complete search history.

(56) References Cited

U.S. PATENT DOCUMENTS

2008/0275349 A1* 11/2008 Halperin ................ A61B 5/447
600/484
2013/0096393 A1* 4/2013 Osorio ................... A61B 5/048
600/301
(Continued)

FOREIGN PATENT DOCUMENTS

JP 2004-357758 A 12/2004
JP 2005-066045 A 3/2005
(Continued)

OTHER PUBLICATIONS

International Search Report for related International Application No. PCT/JP2016/052830, dated Apr. 26, 2016; English translation provided; 4 pages.

*Primary Examiner* — Andrey Shostak
(74) *Attorney, Agent, or Firm* — Procopio, Cory, Hargreaves & Savitch LLP

(57) ABSTRACT

A biological sound analyzing apparatus is provided with: an obtaining device configured to obtain biological sound information, which indicates a change in biological sounds with time; a first calculating device configured to calculate first information, which indicates a variation degree based on a first reference value of the biological sounds in a first period, on the basis of the biological sound information; a second calculating device configured to calculate second information, which indicates a variation degree based on a second reference value of the biological sounds in a second period, on the basis of the biological sound information, wherein the second period is longer than the first period; and an output-
(Continued)

ting device configured to output noise information, which indicates noise included in the biological sounds, on the basis of the first information and the second information. This makes it possible to preferably analyze the noise included in the biological sounds.

5 Claims, 6 Drawing Sheets

(51) Int. Cl.
*A61B 5/00* (2006.01)
*A61B 7/00* (2006.01)

(52) U.S. Cl.
CPC ........ *A61B 7/04* (2013.01); *A61B 2562/0204* (2013.01)

(56) References Cited

U.S. PATENT DOCUMENTS

| 2014/0228692 A1* | 8/2014 | Chan | A61B 5/0472 600/484 |
| 2015/0201879 A1* | 7/2015 | Hargrove | A61B 5/0484 600/411 |

FOREIGN PATENT DOCUMENTS

| JP | 2009-106574 A | 5/2009 |
| JP | 2014-090722 A | 5/2014 |

* cited by examiner

BIOLOGICAL SOUND ANALYZING APPARATUS, BIOLOGICAL SOUND ANALYZING METHOD, COMPUTER PROGRAM, AND RECORDING MEDIUM

CROSS-REFERENCE TO RELATED APPLICATIONS

This application is a U.S. National Stage entry of PCT Application No: PCT/JP2016/052830 filed Jan. 29, 2016, the contents of which are incorporated herein by reference.

TECHNICAL FIELD

The present invention relates to a biological sound analyzing apparatus and a biological sound analyzing method for analyzing biological sounds, which may include adventitious sounds, a computer program, and a recording medium.

BACKGROUND ART

For this type of apparatus, there is known an apparatus configured to distinguish sound types of adventitious sounds, i.e., sounds that are different from normal breath sounds, wherein the adventitious sounds are included in breath sounds of a living body detected by an electronic stethoscope or the like. For example, in Patent Literature 1, there is proposed a technology/technique in which abnormal sounds are detected by analyzing spectral information of biological sounds. In Patent Literature 2, there is proposed a technology/technique in which abnormal sounds are detected by using Hilbert transformation.

CITATION LIST

Patent Literature

Patent Literature 1: Japanese Patent Application Laid Open No. 2005-066045
Patent Literature 2: Japanese Patent Application Laid Open No. 2009-106574

SUMMARY OF INVENTION

Technical Problem

In the technology/technique described in the Patent Literature 1 described above, the abnormal sounds are detected by analyzing the spectral information of the biological sounds; however, in some abnormal sounds, e.g., discontinuous sounds or crackles or the like, a characteristic feature hardly appears on their spectra. Thus, depending on the types of the abnormal sounds included in the biological sounds, even if the spectral information is analyzed, information about the abnormal sounds cannot be accurately detected, which is technically problematic. Moreover, in the technology/technique described in the Patent Literature 2, an apparatus has a large processing load because the Hilbert transformation is used, which is technically problematic.

An example of problems to be solved by the present invention includes the aforementioned technical problems. It is therefore an object of the present invention to provide a biological sound analyzing apparatus and a biological sound analyzing method in which the adventitious sounds included in the biological sounds can be preferably analyzed, a computer program, and a recording medium.

Solution to Problem

The above object of the present invention can be achieved by a biological sound analyzing apparatus provided with: an obtaining device configured to obtain biological sound information, which indicates a change in biological sounds with time; a first calculating device configured to calculate first information, which indicates a variation degree based on a first reference value of the biological sounds in a first period, on the basis of the biological sound information; a second calculating device configured to calculate second information, which indicates a variation degree based on a second reference value of the biological sounds in a second period, on the basis of the biological sound information, wherein the second period is longer than the first period; and an outputting device configured to output noise information, which indicates noise included in the biological sounds, on the basis of the first information and the second information.

The above object of the present invention can be achieved by a biological sound analyzing method provided with: an obtaining process of obtaining biological sound information, which indicates a change in biological sounds with time; a first calculating process of calculating first information, which indicates a variation degree based on a first reference value of the biological sounds in a first period, on the basis of the biological sound information; a second calculating process of calculating second information, which indicates a variation degree based on a second reference value of the biological sounds in a second period, on the basis of the biological sound information, wherein the second period is longer than the first period; and an outputting process of outputting noise information, which indicates noise included in the biological sounds, on the basis of the first information and the second information.

The above object of the present invention can be achieved by a computer program product for making a computer perform: an obtaining process of obtaining biological sound information, which indicates a change in biological sounds with time; a first calculating process of calculating first information, which indicates a variation degree based on a first reference value of the biological sounds in a first period, on the basis of the biological sound information; a second calculating process of calculating second information, which indicates a variation degree based on a second reference value of the biological sounds in a second period, on the basis of the biological sound information, wherein the second period is longer than the first period; and an outputting process of outputting noise information, which indicates noise included in the biological sounds, on the basis of the first information and the second information.

The above object of the present invention can be achieved by a recording medium on which the computer program product described above is recorded.

DESCRIPTION OF EMBODIMENTS

<1>

Figure 1:
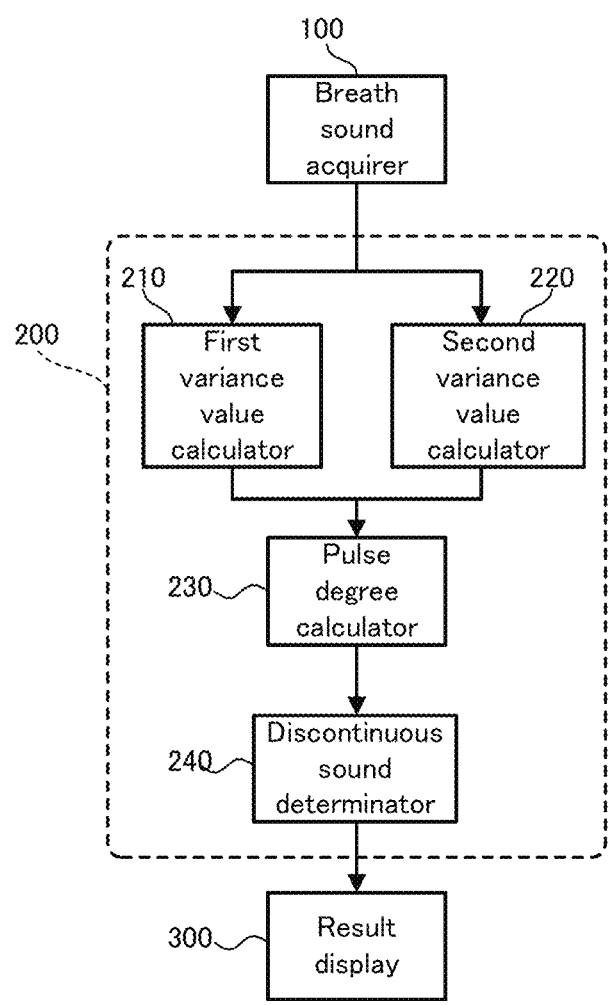
FIG. 1 is a block diagram illustrating a configuration of a biological sound analyzing apparatus according to an example.

A biological sound analyzing apparatus according to an embodiment is provided with: an obtaining device configured to obtain biological sound information, which indicates a change in biological sounds with time; a first calculating device configured to calculate first information, which indicates a variation degree based on a first reference value of the biological sounds in a first period, on the basis of the biological sound information; a second calculating device configured to calculate second information, which indicates a variation degree based on a second reference value of the biological sounds in a second period, on the basis of the biological sound information, wherein the second period is longer than the first period; and an outputting device configured to output noise information, which indicates noise included in the biological sounds, on the basis of the first information and the second information.

According to the biological sound analyzing apparatus in the embodiment, in operation thereof, the biological sound information is firstly obtained by the obtaining device. The "biological sounds" may be sounds generated by a living body, and are typically breath sounds. The "biological sound information" may be information that indicates the change in the biological sounds with time, and may be obtained, for example, as a time-axis waveform indicating the biological sounds.

The biological sounds may include the noise that is not included in normal biological sounds, e.g., discontinuous sounds, which are adventitious sounds, or the like. Thus, the biological sound information, which indicates the biological sounds, may include the noise information, which indicates the noise.

If the biological information is obtained, the first information is calculated by the first calculating device. The first information may be information indicating the variation degree (or a variance value) based on the first reference value of the biological sounds in the first period. Here, the "first period" may be a period set in advance to calculate the first information, and may be set, for example, as a period corresponding to a generation interval of the noise that may be included in the biological sounds. Moreover, the "first reference value" may be a value set as a reference for calculating the variation degree, and may be set at each time as a value that allows the variation degree based on this value to be detected as a pulse degree.

If the biological information is obtained, the second information is further calculated by the second calculating device. The second information may be information indicating the variation degree (or the variance value) based on the second reference value of the biological sounds in the second period, which is longer than the first period. Here, the "second period" may be a period set in advance to calculate the second information, and may be set, for example, as a period corresponding to the generation interval of the noise that may be included in the biological sounds. Moreover, the "second reference value" may be a value set as a reference for calculating the variation degree, and may be set at each time as a value that allows the variation degree based on this value to be detected as the pulse degree.

If the first information and the second information are calculated, the noise information, which indicates the noise, is outputted from the outputting device on the basis of the first and second information. Specifically, on the outputting device, the first information and the second information are used to calculate the pulse degree of the biological sound information. Then, it is determined whether or not the biological sounds include the noise on the basis of the pulse degree of the biological sounds, and information about a sound that is determined to be the noise is outputted as the noise information.

Particularly in the embodiment, the first information and the second information, which indicate the variation degree of the biological sounds, are used to output the noise information. It is thus possible to detect pulse noise (e.g., discontinuous sounds, etc.), which is discontinuously generated. The pulse noise is hardly accurately detected, for example, in spectral analysis of the biological sounds. Specifically, in some cases, the information about the pulse noise may be hidden in the process of time-frequency analysis or the like. Thus, it can be said that the embodiment in which the variation degree of the biological sounds is used to output the noise information is extremely effective to obtain accurate noise information.

Moreover, a process of calculating the first information and the second information and a process of outputting the noise information require a relatively low processing load. The processing load can be effectively reduced in comparison with, for example, Hilbert transformation and Fast Fourier Transform (FFT) or the like.

<2>

In another aspect of the biological sound analyzing apparatus according to the embodiment, the first period is a period included in the second period, and the outputting device is configured to output the noise information on the basis of third information, which is obtained by dividing the first information by the second information.

According to this aspect, the first information may be divided by the second information, by which the third information, which clearly indicates a local variation degree (in other words, the pulse degree) is calculated. Specifically, if there are significant variations in the first period but if the variation degree is small in a period other than the first period, i.e., in a period other than the first period in the second period, then, the third information may be calculated as a large value.

By using the third information, the pulse noise, which is included in the biological sounds and which is discontinuously generated, can be distinguished. It is therefore possible to output more accurate noise information.

<3>

In another aspect of the biological sound analyzing apparatus according to the embodiment, the biological sound information is breath sound information, which indicates breath sounds of a living body, and the noise is adventitious sounds included in the breath sounds.

According to this aspect, it is possible to output the noise information about the adventitious sounds (which are particularly discontinuous sounds) included in the breath sounds, by analyzing the obtained breath sound information.

<4>

In an aspect in which the noise information included in the breath sounds is outputted, as described above, the outputting device may be configured to output the noise information, which indicates that discontinuous sounds are included in the biological sounds in the first period, if the third information is greater than or equal to a first threshold value.

In this case, by comparing the third information, i.e., the information obtained by dividing the first information by the second information, with the first threshold value, it is possible to easily and accurately determine whether or not the discontinuous sounds are included in the biological sounds. The "first threshold value" may be a value set as a threshold value for distinguishing between the discontinuous sounds and the other sounds. Sounds in which the third information is greater than or equal to the first threshold value may be determined to be the discontinuous sounds, and sounds in which the third information is less than the first threshold value may be determined to be the sounds other than the discontinuous sounds.

By using the aforementioned determination results, it is possible to output the accurate noise information about the discontinuous sounds.

<5>

Alternatively, in an aspect in which the noise information included in the breath sounds is outputted, as described above, the outputting device may be configured to calculate a ratio in which the third information is greater than or equal to the first threshold value, in one breathing cycle, and is configured to output the noise information, which indicates that discontinuous sounds are included in the biological sounds in the first period, if the ratio is greater than or equal to a second threshold value.

In this case, it is determined whether or not sounds are the discontinuous sounds in accordance with a result of comparison between the ratio in which the third information is greater than or equal to the first threshold value in one breathing cycle, and the second threshold value. The "second threshold value" may be a value set as a threshold value for distinguishing between the discontinuous sounds and the other sounds. Sounds in which the calculated ratio is greater than or equal to the second threshold value may be determined to be the discontinuous sounds, and sounds in which the calculated ratio is less than the second threshold value may be determined to be the sounds other than the discontinuous sounds.

By using the ratio in one breathing cycle as described above, it is possible to understand the pulse degree, more accurately, than when instantaneous information is used. It is therefore possible to output the more accurate noise information about the discontinuous sounds.

<6>

A biological sound analyzing method according to an embodiment is provided with: an obtaining process of obtaining biological sound information, which indicates a change in biological sounds with time; a first calculating process of calculating first information, which indicates a variation degree based on a first reference value of the biological sounds in a first period, on the basis of the biological sound information; a second calculating process of calculating second information, which indicates a variation degree based on a second reference value of the biological sounds in a second period, on the basis of the biological sound information, wherein the second period is longer than the first period; and an outputting process of outputting noise information, which indicates noise included in the biological sounds, on the basis of the first information and the second information.

According to the biological sound analyzing method in the embodiment, as in the biological sound analyzing apparatus in the embodiment described above, it is possible to output the accurate noise information.

Even the biological sound analyzing method in the embodiment can also adopt the same various aspects as those of the biological sound analyzing apparatus in the embodiment described above.

<7>

A computer program product according to an embodiment makes a computer perform: an obtaining process of obtaining biological sound information, which indicates a change in biological sounds with time; a first calculating process of calculating first information, which indicates a variation degree based on a first reference value of the biological sounds in a first period, on the basis of the biological sound information; a second calculating process of calculating second information, which indicates a variation degree based on a second reference value of the biological sounds in a second period, on the basis of the biological sound information, wherein the second period is longer than the first period; and an outputting process of outputting noise information, which indicates noise included in the biological sounds, on the basis of the first information and the second information.

According to the computer program in the embodiment, it can make a computer to perform the same processes as those in the biological sound analyzing method in the embodiment described above. It is therefore possible to output the accurate noise information.

Even the computer program in the embodiment can also adopt the same various aspects as those of the biological sound analyzing apparatus in the embodiment described above.

<8>

On a recording medium according to an embodiment, the computer program product described above is recorded.

According to the recording medium in the embodiment, it is possible to output the accurate noise information by making a computer perform the computer program described above.

The operation and other advantages of the biological sound analyzing apparatus, the biological sound analyzing method, the computer program, and the recording medium according to the embodiments will be explained in more detail in the following examples.

EXAMPLES

Hereinafter, a biological sound analyzing apparatus, a biological sound analyzing method, a computer program, and a recording medium according to examples will be explained in detail. In the following examples, a biological sound analyzing apparatus configured to analyze breath sounds will be explained.

<Configuration of Apparatus>

Firstly, a configuration of a biological sound analyzing apparatus according to an example will be explained with reference to FIG. 1. FIG. 1 is a block diagram illustrating the configuration of the biological sound analyzing apparatus according to the example.

In FIG. 1, the biological sound analyzing apparatus according to the example is provided with a breath sound acquirer 100, a processor 200, and a result display 300.

The breath sound acquirer 100 may be a sensor configured to obtain breath sounds of a living body as a breath sound signal. The breath sound acquirer 100 is provided with a microphone using e.g., an electrets condenser microphone (ECM) and a piezo microphone, a vibration sensor, and the like. The breath sound acquirer 100 may be the sensor configured to obtain the breath sounds of the living body as the breath sound signal, but also may include a unit configured to obtain the breath sound signal from the sensor. The breath sound signal obtained by the breath sound acquirer 100 may be outputted to a first variance value calculator 210 and a second variance value calculator 220 of the processor 200. The breath sound acquirer 100 is a specific example of the "obtaining device".

The processor 200 may include a plurality of arithmetic circuits and a memory or the like. The processor 200 is provided with the first variance value calculator 210, the second variance value calculator 220, a pulse degree calculator 230, and a discontinuous sound determinator 240.

The first variance value calculator 210 is configured to calculate a first variance value by using breath sound information obtained by the breath sound acquirer 100, wherein the first variance value indicates variations in the breath sound information in a period of t to t+w1. Specifically, the first variance value calculator 210 is configured to set a partial period in the breath sound signal, which is obtained as the breath sound information, as a period with a period width w1 based on each time point t, and is configure to calculate a first variance value $V_{w1}(t)$ in the period of t to t+w1 on the basis of a reference value $\bar{f}_{w_1}(t)$. The first variance value $V_{w1}(t)$ calculated by the first variance value calculator 210 may be outputted to the pulse degree calculator 230. The first variance value calculator 210 is a specific example of the "first calculating device". The first variance value $V_{w1}(t)$ is a specific example of the "first information".

The second variance value calculator 220 is configured to calculate a second variance value by using the breath sound information obtained by the breath sound acquirer 100, wherein the second variance value indicates variations in the breath sound information in a period of t to t+w2. Specifically, the second variance value calculator 220 is configured to set a partial period, i.e., a period including the period of t to t+w1, in the breath sound signal, which is obtained as the breath sound information, as a period with a period width w2 based on each time point t, and is configure to calculate a second variance value $V_{w2}(t)$ in the period of t to t+w2 by using the breath sound signal f(t). The second variance value $V_{w2}(t)$ calculated by the second variance value calculator 220 may be outputted to the pulse degree calculator 230. The second variance value calculator 220 is a specific example of the "second calculating device". The second variance value $V_{w2}(t)$ is a specific example of the "second information".

The first variance value calculator 210 and the second variance value calculator 220 are not necessarily provided as separate arithmetic circuits, and may be configured as a common arithmetic circuit. In other words, one variance value calculator may calculate both the first variance value $V_{w1}(t)$ and the second variance value $V_{w2}(t)$.

The pulse degree calculator 230 is configured to calculate a pulse degree P(t) of the breath sound information by using the first variance value $V_{w1}(t)$ calculated by the first variance value calculator 220 and the second variance value $V_{w2}(t)$ calculated by the second variance value calculator 220. Specifically, the pulse degree calculator 230 is configured to divide the first variance value $V_{w1}(t)$ by the second variance value $V_{w2}(t)$, thereby calculating the pulse degree P(t). The pulse degree P(t) calculated by the pulse degree calculator 230 may be outputted to the discontinuous sound determiantor 240.

The discontinuous sound determiantor 240 is configured to determine whether or not the breath sounds include discontinuous sounds on the basis of the pulse degree P(t) calculated by the pulse degree calculator 230. A specific determination method used by the discontinuous sound determiantor 240 will be detailed in an explanation about operation described later. A determination result of the discontinuous sound determiantor 240 may be outputted to a result display 400, as information about the discontinuous sounds.

The pulse degree calculator 230 and the discontinuous sound determiantor 240 are a specific example of the "outputting device".

As described above, the processor 200 is configured to determine whether or not the biological sounds include the discontinuous sounds, on the basis of the breath sound information obtained by the breath sound acquirer 200. The processor 200 may not only be configured to determine whether or not the biological sounds include the discontinuous sounds, but also be configured to output the intensity of the discontinuous sounds, or the like.

The result display 400 is configured as a display, such as, for example, a liquid crystal monitor, and is configured to display various information outputted from the processor 200 as image data.

<Characteristics of Discontinuous Sounds>

Figure 2:
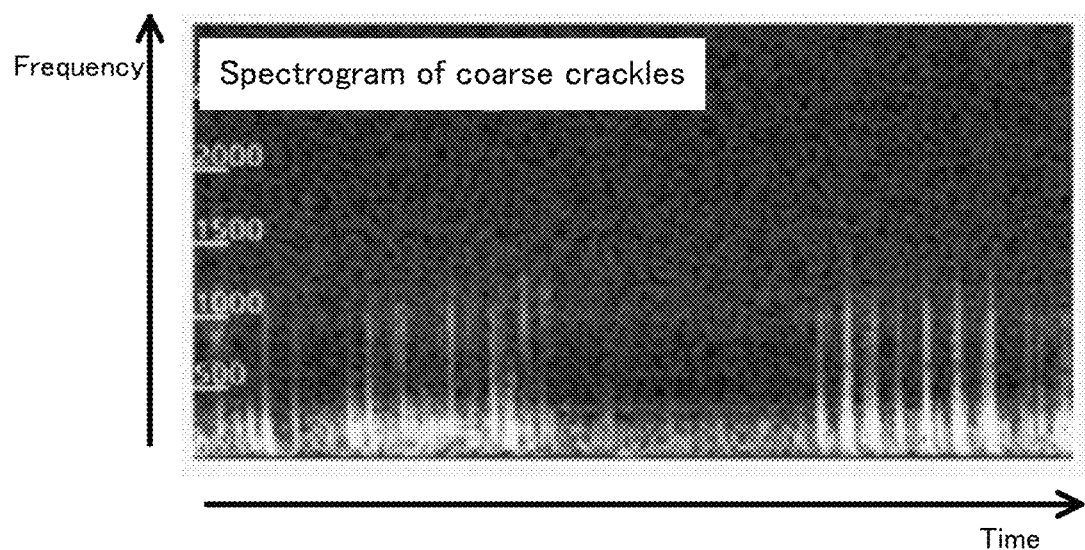
FIG. 2 is a diagram illustrating an example of a spectrogram of coarse crackles.
Figure 3:
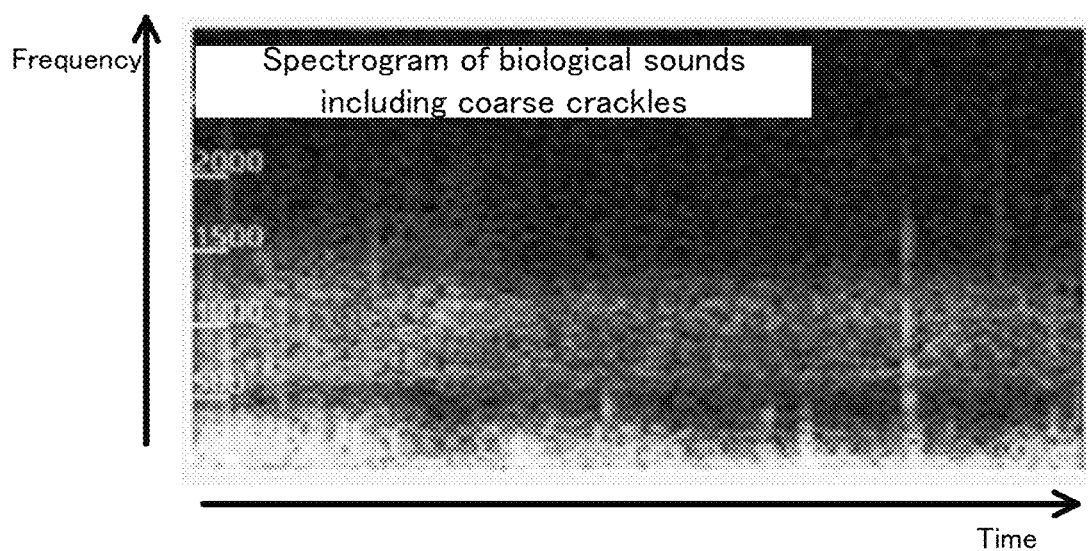
FIG. 3 is a diagram illustrating an example of a spectrogram of biological sounds including coarse crackles.

Next, characteristics of the discontinuous sounds determined on the biological sound analyzing apparatus according to the example will be explained in detail with reference to FIG. 2 and FIG. 3. FIG. 2 is a diagram illustrating an example of a spectrogram of coarse crackles. FIG. 3 is a diagram illustrating an example of a spectrogram of biological sounds including coarse crackles.

The spectrograms illustrated in FIG. 2 and FIG. 3 are obtained by performing time frequency analysis, such as fast Fourier transform (FFT), on a breath sound waveform; however, a process of obtaining the spectrogram as described above is not necessarily required for the biological sound analyzing apparatus according to the example.

As illustrated in FIG. 2, the coarse crackles, which are a type of the discontinuous sounds, are abnormal sounds that are discontinuously generated. The coarse crackles are abnormal sounds generated in a relatively low frequency band among the discontinuous sounds.

As illustrated in FIG. 3, when viewed as the spectrogram of the biological sounds, the coarse crackles are possibly hidden in the normal biological sounds. In this case, it is hard not only to extract the coarse crackles but also to determine whether the biological sounds include the coarse crackles.

As described above, the discontinuous sounds represented by the coarse crackles are hardly distinguished in the analysis using the spectrogram. In contrast, the biological sound analyzing apparatus according to the example is configured to perform a process, which will be detailed below, thereby distinguishing the discontinuous sounds included in the biological sounds.

<Explanation of Operation>

Figure 4:
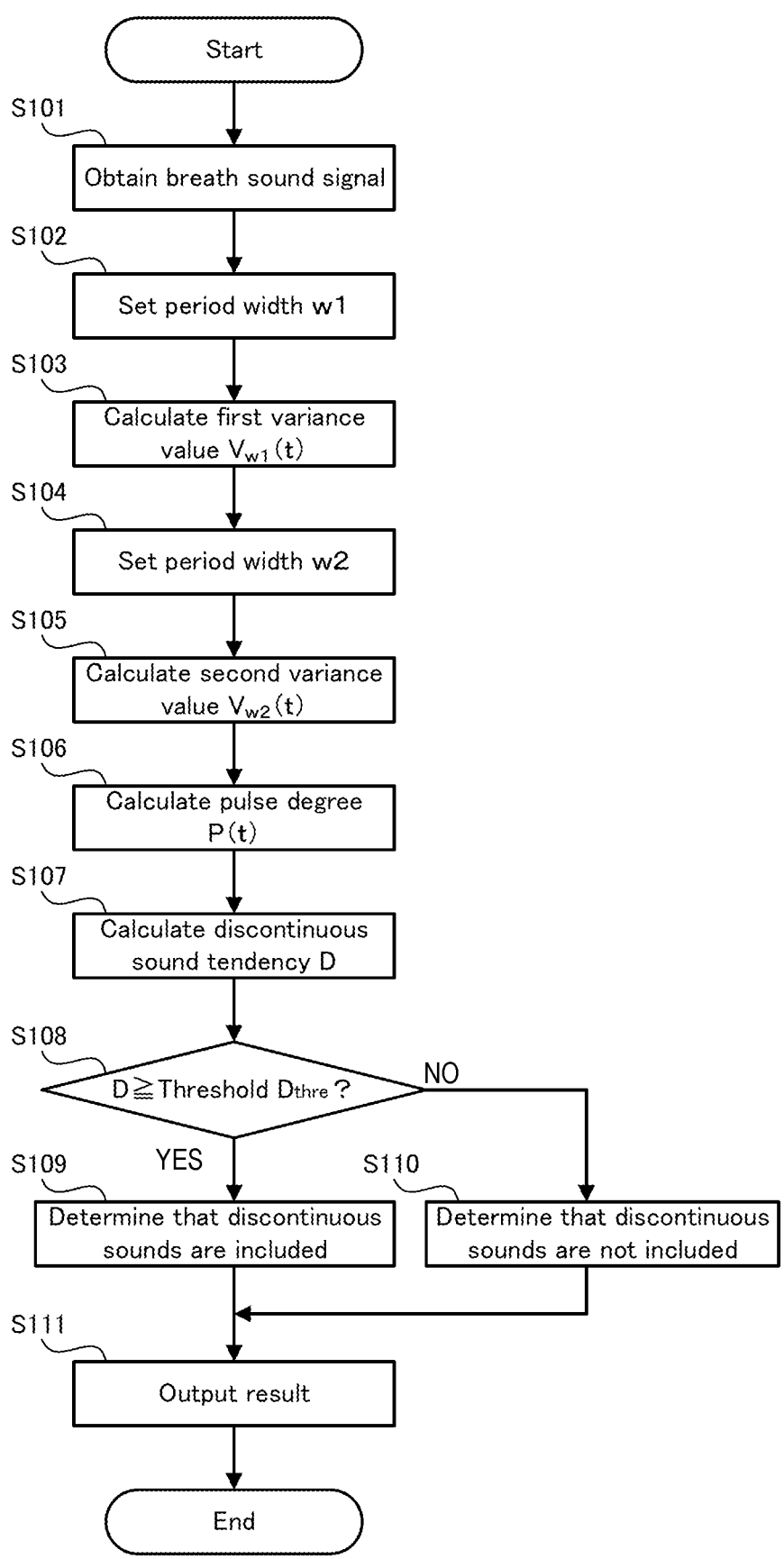
FIG. 4 is a flowchart illustrating a flow of operations of the biological sound analyzing apparatus according to the example.
Figure 5:
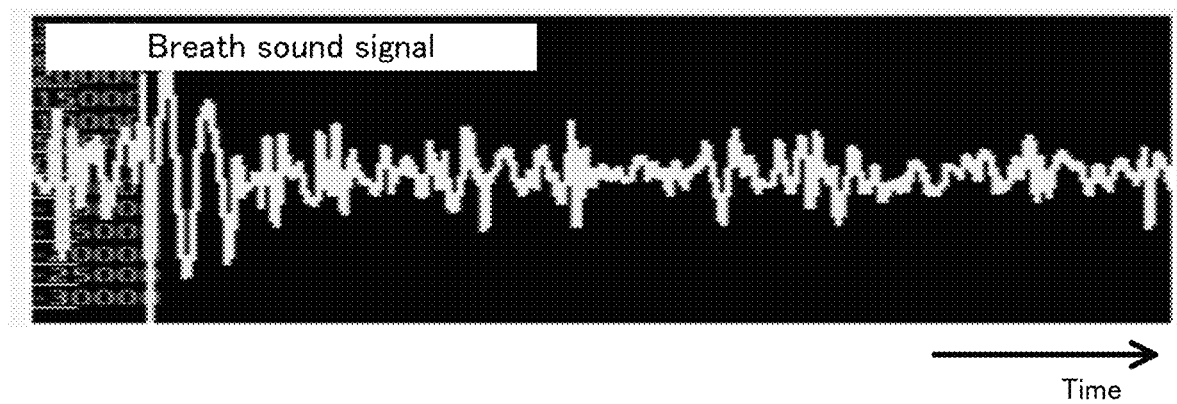
FIG. 5 is a graph illustrating an example of a time-axis waveform of a breath sound signal.
Figure 6:
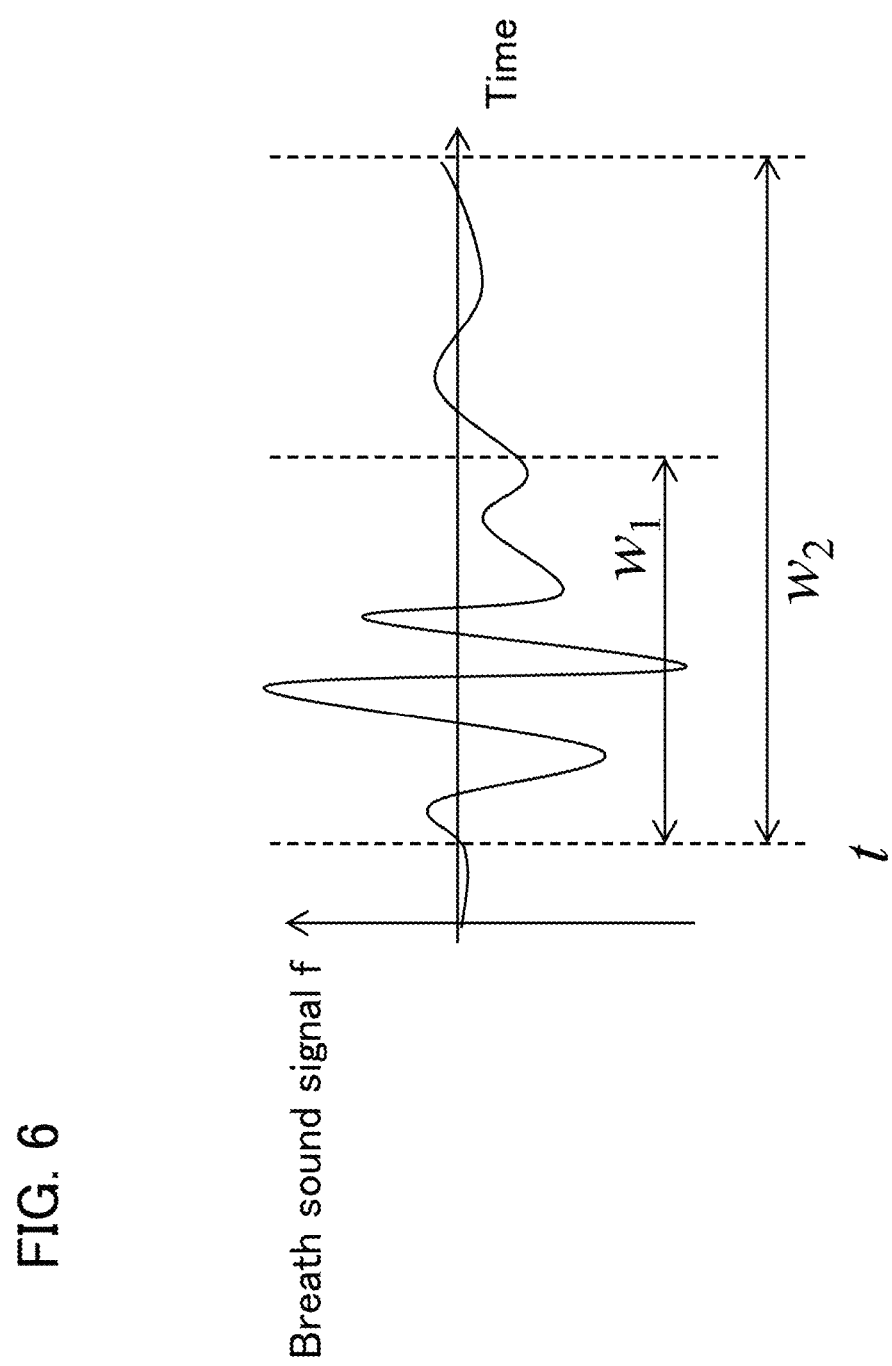
FIG. 6 is a conceptual diagram illustrating a method of calculating a first variance value and a second variance value.
Figure 7:
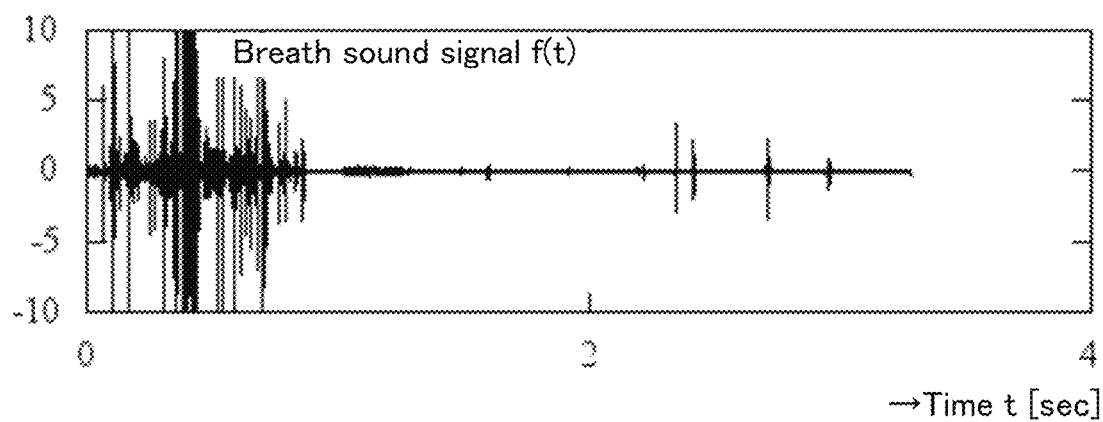
FIG. 7 is a graph illustrating a waveform example of the breath sound signal.
Figure 8:
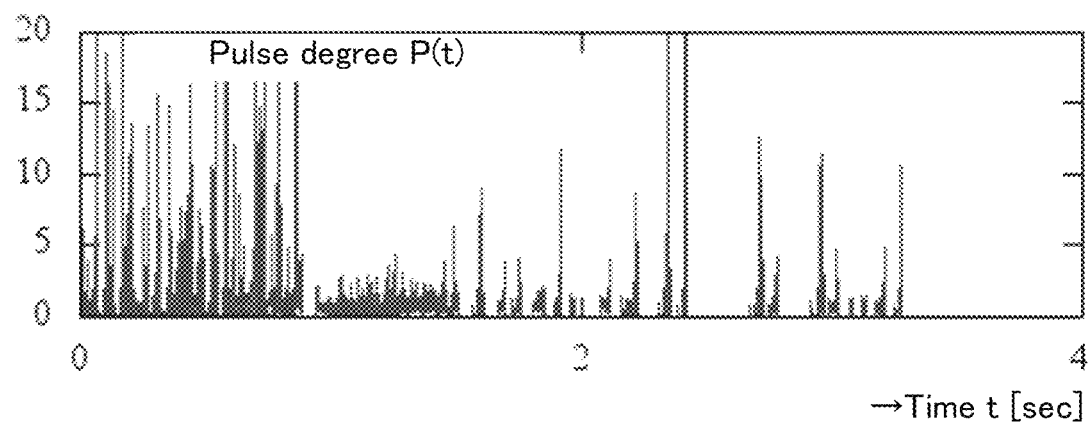
FIG. 8 is a graph illustrating an example of a pulse degree calculated from the breath sound signal.

Next, operations of the biological sound analyzing apparatus according to the example will be explained with reference to FIG. 4 to FIG. 8. FIG. 4 is a flowchart illustrating a flow of the operations of the biological sound analyzing apparatus according to the example. FIG. 5 is a graph illustrating an example of a time-axis waveform of the breath sound signal. FIG. 6 is a conceptual diagram illustrating a method of calculating the first variance value and the second variance value. FIG. 7 is a graph illustrating a waveform example of the breath sound signal. FIG. 8 is a graph illustrating an example of a pulse degree calculated from the breath sound signal.

In FIG. 4, in operation of the biological sound analyzing apparatus according to the example, firstly, the breath sound signal indicating the breath sounds of the living body is obtained on the breath sound acquirer 100 (step S101). The breath sound signal may be obtained as a waveform indicating a temporal variation in the breath sounds (refer to FIG. 5).

If the breath sound signal is obtained, the period with the period width w1, which is a calculation target section, is set on the first variance value calculator 210 (step S102). Then, on the first variance value calculator 210, variations in the breath sound signal in the period with the period width w1 based on each time point t are calculated as the first variance value $V_{w1}(t)$ (step S103).

In the same manner, on the second variance value calculator 220, the period with the period width w2, which is a calculation target section, is set on the second variance value calculator 220 (step S104). Then, on the second variance value calculator 220, variations in the breath sound signal in the period with the period width w2 based on each time point t are calculated as the second variance value $V_{w2}(t)$ (step S105).

If the first variance value $V_{w1}(t)$ and the second variance value $V_{w2}(t)$ are calculated, the pulse degree P(t) is calculated on the pulse degree calculator 230 (step S106).

Hereinafter, a method of calculating the first variance value $V_{w1}(t)$, the second variance value $V_{w2}(t)$, and the pulse degree P(t) will be explained, more specifically.

As illustrated in FIG. 6, the period of t to t+w2 may be set as a period including the period of t to t+w1. In the example, the reference value $\bar{f}_{w_1}(t)$ for calculating the first variance value $V_{w1}(t)$ is different from a $\bar{f}_{w_2}(t)$ for calculating the second variance value $V_{w2}(t)$. The reference value for calculating the first variance value $V_{w1}(t)$, however, may be the same as the reference value for calculating the second variance value $V_{w2}(t)$. In order that the pulse degree P(t) described later has an appropriate value, it is preferable that the two reference values are not significantly different from each other.

The pulse degree P(t) may be calculated by dividing the first variance value $V_{w1}(t)$ by the second variance value $V_{w2}(t)$. Specifically, the following equations (1) to (3) can be used for the calculation.

[Equation 1]

$$P(t) = \frac{V_{w_1}(t)}{V_{w_2}(t)} = \frac{\frac{1}{w_1}\int_t^{t+w_1}(f(\tau) - \bar{f}_{w_1}(t))^2 d\tau}{\frac{1}{w_2}\int_t^{t+w_2}(f(\tau) - \bar{f}_{w_2}(t))^2 d\tau} \quad (1)$$

[Equation 2]

$$\bar{f}_{w_1}(t) = \frac{1}{w_1}\int_t^{t+w_1} f(\tau)d\tau \quad (2)$$

[Equation 3]

$$\bar{f}_{w_2}(t) = \frac{1}{w_2}\int_t^{t+w_2} f(\tau)d\tau \quad (3)$$

The aforementioned equations are merely an example. The first variance value $V_{w1}(t)$, the second variance value $V_{w2}(t)$, and the pulse degree P(t) can be calculated by using different equations.

More specifically, if the breath sound signal as illustrated in FIG. 7 is obtained, the pulse degree P(t) as illustrated in FIG. 8 is calculated. As is clear from the drawings, the pulse degree P(t) is high in a part in which the breath sound signal significantly varies. From this, it can be said that the pulse degree P(t) is a value indicating local variations in a signal power.

Back in FIG. 4, if the pulse degree P(t) is calculated, a discontinuous sound tendency D is calculated on the discontinuous sound determinator 240 (step S107).

For the calculation of the discontinuous sound tendency D, a function g(t) expressed by the following equation (4) is used.

[Equation 4]

$$g(t) = \begin{cases} 1 & P(t) \geq P_{thre} \\ 0 & P(t) < P_{thre} \end{cases} \quad (4)$$

As is clear from the aforementioned equations, the function g(t) has a value "1" when the pulse degree P(t) is greater than or equal to a threshold value $P_{thre}$, and has a value "0" when the pulse degree P(t) is less than the threshold value $P_{thre}$. The threshold value $P_{thre}$ may be a threshold value for determining whether or not the pulse degree P(t) is high enough to determine that the breath sounds include the discontinuous sounds, and an appropriate value may be obtained and set in advance. The threshold value $P_{thre}$ is a specific example of the "first threshold value".

The discontinuous sound tendency can be calculated from the following equation (5) by using the function g(t).

[Equation 5]

$$D = \frac{1}{T}\int_0^T g(t)dt \quad (5)$$

T is a breathing cycle time or a respiratory cycle time.

The discontinuous sound tendency D may be a value indicating a ratio in which the pulse degree P(t) is greater than or equal to the threshold value $P_{thre}$, in one breathing cycle time. It is determined on the discontinuous sound determinator 240 whether or not the calculated discontinuous sound tendency D is greater than or equal to a threshold value $D_{thre}$ (step S108). The threshold value $D_{thre}$ may be a threshold value for determining whether or not the discontinuous sound tendency D is high enough to determine that the breath sounds include the discontinuous sounds, and an appropriate value may be obtained and set in advance. The threshold value $D_{thre}$ is a specific example of the "second threshold value".

On the discontinuous sound determinator 240, if the discontinuous sound tendency D is greater than or equal to the threshold value $D_{thre}$ (the step S108: YES), it is determined that the breath sounds include the discontinuous sounds (step S109). On the other hand, if the discontinuous sound tendency D is less than the threshold value $D_{thre}$ (the step S108: NO), it is determined that the breath sounds do not include the discontinuous sounds (step S110).

In the example, the discontinuous sound tendency D is used to determined whether or not the breath sounds include the discontinuous sounds, but it may be determined that the breath sounds include the discontinuous sounds at a time point at which it is determined that the pulse P(t) is greater than or equal to the threshold value $P_{thre}$.

A determination result about the discontinuous sounds explained above is outputted to the result display 300 (step S111). By this, whether or not the breath sounds include the discontinuous sounds may be displayed as image data on the result display 300.

<Effect of Example>

Lastly, a technical effect obtained by the biological sound analyzing apparatus according to the example will be explained in detail.

According to the biological sound analyzing apparatus in the example, as explained above, it is determined whether or not the breath sounds include the discontinuous sounds, by using the pulse degree P(t) of the breath sound signal and the discontinuous sound tendency D.

According to the determination method described above, for example, even a sound that may be hidden in spectrogram analysis can be accurately distinguished. The determination can be performed in a relatively simple process, so that a processing load can be effectively reduced.

A sound other than the discontinuous sounds can be distinguished on the biological sound analyzing apparatus according to the example as long as it is a sound that shows the same tendency, i.e., a sound characterized by the pulse degree of an obtained signal.

The present invention is not limited to the aforementioned embodiments and examples, but various changes may be made, if desired, without departing from the essence or spirit of the invention which can be read from the claims and the entire specification. A biological sound analyzing apparatus, a biological sound analyzing method, a computer program, and a recording medium that involve such changes are also intended to be within the technical scope of the present invention.

DESCRIPTION OF REFERENCE NUMERALS AND LETTERS 100 breath sound acquirer
200 processor
210 first variance value calculator
220 second variance value calculator
230 pulse degree calculator
240 discontinuous sound determinator
250 result display
w1 first period width
w2 second period width
Vw1(*t*) first variance value
Vw2(*t*) second variance value
P(t) pulse degree
D discontinuous sound tendency

The invention claimed is:

1. A biological sound analyzing apparatus comprising:
a microphone configured to obtain biological sound information as a time-axis waveform, which indicates a change in biological sounds with time;
a memory storing a program; and
a processor coupled to the memory and the microphone, the processor configured to execute the program to:
calculate first information, which indicates a variation degree based on a first reference value of the biological sounds in a first period of the time-axis waveform, on the basis of the biological sound information;
calculate second information, which indicates a variation degree based on a second reference value of the biological sounds in a second period of the time-axis waveform, on the basis of the biological sound information, wherein the second period is longer than the first period and the first period is a period included in the second period; and
output noise information, which indicates noise included in the biological sounds in the first period, on the basis of the first information and the second information, and further on the basis of third information, which is obtained by dividing the first information by the second information,
wherein the processor is further configured to:
output the noise information if the third information is greater than or equal to a first threshold value, and if a calculated ratio, in which the third information is greater than or equal to the first threshold value, is greater than or equal to a second threshold value.

2. The biological sound analyzing apparatus according to claim 1, wherein
the biological sound information is breath sound information, which indicates breath sounds of a living body, and
the noise includes adventitious sounds included in the breath sounds.

3. The biological sound analyzing apparatus according to claim 1, wherein the ratio in which the third information is greater than or equal to the first threshold value is calculated for one breathing cycle, wherein the noise includes discontinuous sounds included in the biological sounds in the first period.

4. A biological sound analyzing method comprising:
an obtaining process of obtaining biological sound information as a time-axis waveform, which indicates a change in biological sounds with time;
a first calculating process of calculating first information, which indicates a variation degree based on a first reference value of the biological sounds in a first period of the time-axis waveform, on the basis of the biological sound information;
a second calculating process of calculating second information, which indicates a variation degree based on a second reference value of the biological sounds in a second period of the time-axis waveform, on the basis of the biological sound information, wherein the second period is longer than the first period and the first period is a period included in the second period;
a third calculating process of determining that third information, which is obtained by dividing the first information by the second information, is greater than or equal to a first threshold value;
a fourth calculating process of calculating a ratio in which the third information is greater than or equal to the first threshold value, and determining whether the ratio is greater than or equal to a second threshold value; and
an outputting process of outputting noise information, which indicates noise included in the biological sounds in the first period, on the basis of the first information, the second information, and the third information, including when the third information is greater than or equal to a first threshold value and the ratio is greater than or equal to the second threshold value.

5. A non-transitory computer-readable recording medium storing a computer program that, when executed by a computer, makes the computer perform:

- an obtaining process of obtaining biological sound information as a time-axis waveform, which indicates a change in biological sounds with time;
- a first calculating process of calculating first information, which indicates a variation degree based on a first reference value of the biological sounds in a first period of the time-axis waveform, on the basis of the biological sound information;
- a second calculating process of calculating second information, which indicates a variation degree based on a second reference value of the biological sounds in a second period of the time-axis waveform, on the basis of the biological sound information, wherein the second period is longer than the first period and the first period is a period included in the second period; and
- an outputting process of outputting noise information, which indicates noise included in the biological sounds in the first period, on the basis of the first information and the second information, and further on the basis of third information, which is obtained by dividing the first information by the second information,
- wherein the outputting process further comprises outputting the noise information if the third information is greater than or equal to a first threshold value, and if a calculated ratio, in which the third information is greater than or equal to the first threshold value, is greater than or equal to a second threshold value.

* * * * *